United States Patent [19]

Humbert et al.

[11] 4,137,302

[45] Jan. 30, 1979

[54] COSMETIC COMPOSITION

[75] Inventors: Françoise Humbert; Micheline Davot, both of Paris, France

[73] Assignee: Lever Brothers Company, New York, N.Y.

[21] Appl. No.: 780,378

[22] Filed: Mar. 23, 1977

[30] Foreign Application Priority Data

Apr. 2, 1976 [GB] United Kingdom ............... 13433/76

[51] Int. Cl.$^2$ .......................... A61K 7/00; A61K 7/22; A61K 7/42; A61K 7/025
[52] U.S. Cl. ....................................... 424/47; 424/54; 424/59; 424/60; 424/61; 424/63; 424/64; 424/69; 424/70; 424/71; 424/358; 424/361
[58] Field of Search .................. 424/70, 71, 358, 361, 424/54, 47, 59, 60, 61, 63, 64, 69

[56] References Cited

U.S. PATENT DOCUMENTS 3,149,042  9/1964  Habicht et al. ..................... 424/70

OTHER PUBLICATIONS

Chemical Abstracts, vol. 70, item 71012m, (1969), which abstracts Brit. 1,142,220.

*Primary Examiner*—Donald B. Moyer
*Attorney, Agent, or Firm*—James J. Farrell; Melvin H. Kurtz; Kenneth F. Dusyn

[57] ABSTRACT

A cosmetic composition for the treatment of human skin comprises monoacetyl urea dispersed or dissolved in a vehicle other than water. The composition may form a liquid or a solid.

2 Claims, No Drawings

COSMETIC COMPOSITION

The invention relates to skin treating compositions and in particular to compositions which exert a moisturising effect on the skin, thereby softening the stratum corneum.

A soft and supple skin has a marked cosmetic appeal and is an attribute of normal functioning epidermis. The outer layer of the epidermis, i.e. the stratum corneum, can however become dry and flaky following exposure to adverse conditions due to loss of water with the result that the skin loses its soft supple characteristics. Emollients such as fats, phospholipids and sterols have in the past been used to soften dry skin, but more recently it has become apparent that these emollients are only partially effective as a remedy for this type of condition.

It is therefore evident that there exists a need for an effective treatment for skin which is in a dry, flaky condition.

Application to the skin of classical humectants is unlikely to alleviate this problem since they are generally rinsed from the skin during washing and for this reason they are not particularly skin substantive.

Even so, it has been proposed that urea can have a softening and moisturising action on dry, flaky skin when applied to the skin, for example as an aqueous solution or in the form of a cream. It does however suffer from the drawback that it tends to be unstable in products of this sort since it decomposes during storage with the release of ammonia.

We have now shown that the relatively short-lived softening and moisturising benefits of urea can be prolonged by employing instead of urea a special derivative thereof which is furthermore stable under conditions of storage and use and in particular does not breakdown with the release of ammonia.

Accordingly, the invention provides a composition for skin treatment comprising from 1 to 99% by weight of monoacetyl urea, together with a cosmetically acceptable vehicle other than water.

The invention is thus based on the discovery that monoacetyl urea can be applied to the skin, together with a suitable vehicle, in order to effect an improvement in the skin or to prevent a deterioration in the condition of the skin, as described herein.

Mono-acetyl urea should be present in the composition according to the invention as a solution, suspension or dispersion in liquid or solid form, depending upon the nature of the composition, but in any case the quantity present will lie between about 1% and 95%. Usually, when the composition is in the form of a liquid, the quantity of mono-acetyl urea will normally be from 1 to 20%, whereas when the composition is a solid such as a cosmetic stick, the proportion of mono-acetyl urea present will normally be from about 1% to about 50%, or even higher. Finely-divided powdered compositions can contain from 1% to 99% by weight of mono-acetyl urea.

It should be explained that use of less than 1% of monoacetyl urea by weight of the composition will not enable the user to obtain any noticeable benefit, whereas the above defined upper limits, depending on the type of composition, are more dictated by the nature of the formulation than by any upper limit to the efficacy of monoacetyl urea as a skin benefit agent.

Following the initial discovery that when mono-acetyl urea was applied to human skin, particularly skin in a dry or flaky condition, it was capable of moisturising, softening and otherwise improving the condition of the skin over a prolonged period, it was apparent that many different composition types could be formulated. For example, and without implying any limitation on the scope of the invention, it was realised that mono-acetyl urea could be incorporated in skin creams designed for application to the skin, in make-up products, particularly for application to the face. All such products could be designed either for the treatment of skin which was already in a dry or flaky condition or for prophylactic use in preventing such conditions occuring. It was further realised that mono-acetyl urea could be employed beneficially in other cosmetic products such as sunscreen products, hair treatment products and oral hygiene products, including mouthwashes and dentifrices.

It follows from this original concept that the provision of a vehicle for mono-acetyl urea in the products of the invention presents a wide range of possibilities. Suitable vehicles can be classified as described hereinafter.

It should be explained that vehicles are substances which can act as diluents, dispersants or carriers for mono-acetyl urea and which therefore ensure that it can be applied to and distributed evenly over the skin at an appropriate concentration; in certain cases, the vehicle can aid its penetration through the stratum corneum into the epidermis, thus ensuring that the effectiveness of the applied mono-acetyl urea is prolonged. It is not intended that water, which can act as a vehicle, is to be excluded; water can certainly be present in many of the compositions according to the invention, but it is intended that these compositions should also contain at least one vehicle other than water.

The vehicles that can be used in compositions according to the invention can include powder absorbents, binders and carriers, and liquids such as emollients, propellants, solvents, humectants and thickeners. Examples of each of these types of vehicles are as follows:

Powder absorbents

Magnesium silicate
Lanolin absorption base
Amorphous silica powder

Powder binders and carriers

Microcrystalline cellulose
Isostearyl neopentanoate
Polyacrylamide
Lauryl lactate
Precipitated silica
Talc
Chalk

Emollients

Stearyl alcohol
Glyceryl monoricinoleate
Glyceryl monostearate
Sulphated tallow
Propylene glycol
Mink oil
Cetyl alcohol
Stearyl stearate
Isopropyl isostearate
Dimethyl brassylate Stearic acid
Isobutyl palmitate
Isocetyl stearate
Oleyl alcohol
Isopropyl laurate
Hexyl laurate
Decyl oleate
Di-isopropyl adipate
2-octadodecanol
Iso-cetyl alcohol
Myristyl ethoxymyristate
Cetyl palmitate
Dimethylpolysiloxane
Di-isopropyl adipate
Di-n-butyl sabacate
Di-isopropyl sebacate
Di-2-ethyl hexyl sebacate
2-ethyl hexyl palmitate
Isononyl isononanoate
Isodecyl isononanoate
Isotridecyl isononanoate
2-ethyl hexyl palmitate
2-ethyl hexyl stearate
Di-(2-ethyl hexyl) adipate
Di-(2-ethyl hexyl) succinate
Isopropyl myristate
Isopropyl palmitate
Isopropyl stearate
Butyl stearate
Glyceryl monostearate
Polyethylene glycols
Propylene glycol
Triethylene glycol
Lanolin
Castor oil
Acetylated lanolin alcohols
Acetylated lanolin
Petrolatum
Isopropyl ester of lanolin fatty acids
Mineral oils
Butyl myristate
Isostearic acid
Palmitic acid
Isopropyl linoleate
Cetyl lactate
Lauryl lactate
Myristyl lactate
Quaternised hydroxy alkyl aminogluconate
Decyl oleate
Isodecyl oleate
Di-isopropyl adipate
2-ethyl hexyl palmitate
Isostearyl neo pentanoate
Myristyl myristate
Di-isopropyl adipate
Oleyl ethoxy myristate
Diglycol stearate
Ethylene glycol monostearate
Myristyl stearate
Isopropyl lanolate

Propellants

Trichlorofluoro methane
Dichloro difluoro methane
Dichloro tetrafluoro ethane
Monochloro difluoro methane
Trichloro trifluoro ethane
Propane
Butane
Isobutane
(used singly or in admixture)

Solvents

Ethyl alcohol
2-ethylhexanol
Ethylene carbonate
Propylene carbonate
N-methyl glucamine
Castor oil
Linear ethoxylated polymer of methanol
Ethylene glycol monoethyl ether
Diethylene glycol monobutyl ether
Diethylene glycol monoethyl ether
Propoxylated butanol
Propoxylated oleyl alcohol
Butyl stearate
Butyl myristate

Humectants

Glycerin
Sorbitol
Sodium 2-pyrrolidone-5-carboxylate
Soluble collagen
Dibutyl phthalate
Gelatin
Polyglycerogen
Ethoxylated (10–20 moles) glucose
Propoxylated (10–20 moles) glucose

Thickeners

Gums
Starch
Colloidal silicon dioxide
Sodium polyacrylate
Tetra alkyl and/or trialkyl aryl ammonium smectites
Chemically modified magnesium aluminium silicate
Organically modified montmorillonite clay
Hydrated aluminium silicate
Fumed silica
Carboxy vinyl polymer
Sodium carboxymethyl cellulose
Hydrocyethyl stearate amide
Ethylene glycol monostearate The quantity of vehicle employed can constitute the balance of the product, or a smaller proportion than the balance, provided that the vehicle is capable of performing, if necessary in admixture with other vehicles, its function as herein defined.

The compositions according to the invention can contain ingredients other than those already mentioned, depending on the form of the intended product. It is, for example, possible to include moisturisers, antiseptics or preservatives, antioxidants, anti-caking agents, emulsifiers, perfumes and colouring agents. Examples of some of the ingredients are as follows:

Moisturisers

Sodium pyrollidone carboxylate
Sodium lactate
Orotic acid,

Antiseptics and preservatives

Cetyl pyridinium chloride
Triboromosalicylanilide
Benzalkonium chloride

Dehydroacetic acid,

Antioxidants

Tocopherol
Ascorbyl palmitate
Propyl gallate
Butylated hydroxy toluene
Butylated hydroxyanisole

Anti-caking agents

Hydrophobic starch
Sulphonated formaldehyde
Silicone dioxide

Anionic emulsifiers

Potassium stearate
Sodium stearate
Ammonium stearate
Triethanolamine stearate
Glyceryl monostearate containing either potassium or sodium soap
Sodium lauryl sulphate
Sodium cetyl sulphate
Glyceryl monostearate containing sodium lauryl sulphate

Cationic emulsifiers

N(stearoyl colamino formylmethyl) pyridinium chloride
N-soya-N-ethyl morpholinium ethosulphate
Alkyl dimethyl benzyl ammonium chloride Di-isobutylphenoxyethoxy ethyl dimethyl benzyl ammonium chloride
Cetyl pyridinium chloride; and

Nonionic emulsifiers

Fatty acid esters of sorbitan anhydrides or ethylene oxide products of sorbitan fatty acid esters such as Span 80 or Tween 80; and pluronics which are addition products of hydrophilic polyoxy ethylene groups and a hydrophilic polyoxy propylene.

The amount of emulsifiers, if used, usually forms from 1 to 10%, preferably 1 to 5% by weight of the composition.

The benefit to the skin following topical application of the compositions can be assessed by measuring the impedence of the skin before and after application.

Thus, we have found that skin which has received a topical application of such a composition has a lower impedence than untreated skin, thus indicating that the treated skin has become moisturised by this treatment.

One method of measuring skin impedence that can be employed is that described by E J Clar, C P Her and C G Sturelle in the "Journal of the Society of Cosmetic Chemists" for July 1975, Volume 26, No 7 at pages 337-353.

An example illustrating the technique employed in this test and some sample results obtained is set out below.

Measurement of skin moisturisation

The ability of a substance to moisturise the skin is assessed by impedance which occurs on the skin which has been treated by the substance.

In this experiment, impedance measurements were made under controlled atmospheric conditions of 66% relative humidity at a temperature of 23° C. The test compared the effectiveness of three skin moisturisers each dissolved in N-methylglucamine against a control containing only this solvent.

The following solutions were compared:

|  | A | B | C | D | E |
|---|---|---|---|---|---|
|  | % by weight | | | | |
| N-methyl glucamine | 4 | 4 | 4 | 4 | 4 |
| Urea | — | 2 | 5 | — | — |
| Acetyl uea | — | — | — | 2 | — |
| Urea pyrollidone carboxylate | — | — | — | — | 2 |
| Water | 96 | 94 | 91 | 94 | 94 |

Each of the solutions A to E was applied to a different area of skin; a further zone of skin (F) was demarcated as a control which received no treatment.

Rats were used as the test animals for evaluation of the efficacy of each solution. The experiments were statistically designed on the basis of a 6 × 6 latin square and Duncan Method (see Duncan DB, Biometrics, March 1975 page 1) was used to evaluate the results.

The mean impedence results obtained by using the method of Clar et al referred to above were as follows:

| C | D | B | E | A | F |
|---|---|---|---|---|---|
| −64 | −52.6 | −35.5 | −35.25 | −16.3 | −6.5 |

The analysis of variance can be summarised as follows:

| Origin of the fluctuations | dde | Mean squares | F |
|---|---|---|---|
| Treatments | 5 | 2761 | 3.7* |
| Zones | 5 | 1905 | |
| Subjects | 5 | 3006 | |
| Error | 20 | 780 | |

*$p < 0.05$
Standard error: $Sm = 11:8 (n^2 = 20)$

The following table sets out an interpretation of the results according to Duncan.

| P | (2) | (3) | (4) | (5) | (6) | |
|---|---|---|---|---|---|---|
| G | 2.95 | 3.25 | 3.18 | 3.10 | 2.95 | |
| RP | 34.81 | 36.58 | 37.52 | 38.33 | 38.94 | |
| | −64 | −52.6 | −35.5 | −35.25 | −16.3 | −6.3 |
| C | D | | B | E | A | F |

Note that any two mean values underlined are not significantly different from each other.

From these results, it is accordingly possible to distinguish two groups of products, the first group comprising urea pyrollidone carboxylate (2%), the solvent, the untreated skin zone, the the second group comprising urea pyrollidone carboxylate (2%), urea (5%) and acetyl urea (2%). Only urea (5%) and acetyl urea (2%) as an aqueous solution in N-methyl glucamine produced a significant fall in impedence as compared with the controls.

It is also apparent that mono acetyl urea at a concentration of 2% has virtually the same effectiveness as a skin moisturiser as urea at a concentration of 5%.

The invention will now be illustrated by reference to the following examples.

EXAMPLE 1

This example illustrates the preparation of make-up powder.

A water phase was prepared by mixing together the following ingredients.

|  | % w/w |
|---|---|
| Mono-acetyl urea | 3 |
| Water | 20 |
| Methanol | 77 |

An oil phase was similarly prepared by mixing together the following ingredients.

|  | % w/w |
|---|---|
| Mineral oil | 60 |
| Decyl oleate | 20 |
| Myristyl alcohol | 5 |
| Isostearic acid | 3 |
| Isopropyl palmitate | 4 |
| Olive oil | 8 |

To 100 parts of the water phase was added 9 parts by weight of the oil phase at a temperature of 10° C. A white precipitate formed. The following ingredients were then added and the whole blended to form a make-up powder.

|  | Parts by weight |
|---|---|
| Talc | 10 |
| Kaolin | 2.5 |
| Zinc oxide | 2.5 |
| Titanium dioxide | 3 |
| Burnt Sienna | 2 |
| Mono-acetyl urea | 15 |

EXAMPLE 2

This example illustrates the preparation of an aerosol lotion.

The following ingredients were employed to form an aerosol lotion.

|  | Parts by weight |
|---|---|
| Polyethylene glycol 1000 monostearate | 2.4 |
| Lanolin alcohols | 1.0 |
| Linear alcohol lactate | 2.0 |
| Myristyl myristate | 1.5 |
| Mineral oil 65/75 | 3.8 |
| Mono-acetyl urea | 2.0 |
| Cationic detergent | ? |
| Water | 64.8 |
| Alcohol | 12.0 |
| Propellant 12/114 (40:60) | 12.0 |

Procedure

Add B to A at 75° C. Cool with agitation to 45° C then add alcohol. Pressure fill and add perfume to suit.

EXAMPLE 3

This example illustrates the preparation of a face cream.

The face cream was prepared from the following ingredients.

| i) Oil phase | % w/w |
|---|---|
| Stearic acid | 18.0 |
| Mineral oil | 5.0 |
| Polyoxyethylene (20) polypropylene glycol monostearate | 5.0 |
| Propyl-p-hydroxy benzoate | 0.05 |

| ii) Aqueous phase | % w/w |
|---|---|
| Propylene glycol | 5.0 |
| 2-pyrrolidone-5-carboxylic acid | 5.0 |
| Sodium hydroxide | 1.6 |
| Mono-acetyl urea | 2.0 |
| Triethanolamine | 1.0 |
| Methyl-p-hydroxy benzoate | 0.1 |
| Water | to 100 |

EXAMPLE 4

This example illustrates the formulation of a sunscreen cream.

The following ingredients were blended to form a sunscreen cream.

|  | % w/w |
|---|---|
| Stearic acid | 2 |
| Wool alcohol | 1 |
| Cetyl alcohol | 3.5 |
| Polar wax, a polyoxyethylene ester of sorbitan | 5 |
| Arachis oil | 15 |
| Ethyl-p-dimethylaminobenzoate |  |
| Ethyl-p-diethylaminobenzoate | 0.75 |
| Butylated hydroxy toluene | 0.02 |
| Glycerin | 3 |
| Sodium citrate | 0.05 |
| Methyl-p-hydroxybenzoate | 0.1 |
| Silicon fluid MS200 | 1 |
| Perfume oil | 0.4 (v/w) |
| Mono-acetyl urea | 8 |
| Water | to 100 |

EXAMPLE 5

This example illustrates the preparation of the formulation of a handcream.

The following ingredients were blended to form a hand cream.

|  | % w/w |
|---|---|
| Isopropyl myristate | 3.0 |
| Polyethylene glycol (1000) monostearate | 5.0 |
| Stearic acid | 19.0 |
| Methyl paraben | 0.15 |
| Polyethylene glycol (300) monostearate | 5.0 |
| Sorbitol | 3.0 |
| Monoacetyl urea | 1.0 |
| Water | 63.85 |
| Perfume and colour | q.s. |

EXAMPLE 6

This example illustrates the formulation of a lipstick.

The following ingredients were blended to form a lipstick.

|  | % w/w |
|---|---|
| Carnauba wax | 10.0 |
| Beeswax | 15.0 |
| Lanolin | 5.0 |
| Cetyl alcohol | 5.0 |
| Caster oil | 64.8 |
| Monoacetyl urea | 5.0 |

EXAMPLE 7

This example illustrates the formulation of an all-purpose mask.

The following ingredients were blended to form an all-purpose mask.

|  | % w/w |
| --- | --- |
| Kaolin | 35.0 |
| Bentonite | 5.0 |
| Cetyl alcohol | 2.0 |
| Sodium lauryl sulphate | 1.0 |
| Glycerin | 10.0 |
| Nipagin M | 0.1 |
| Monoacetyl urea | 5.0 |
| Perfume | q.s. |
| Water | to 100 |

EXAMPLE 8

This example illustrates the formulation of a toothpaste.

The following ingredients were blended to form a toothpaste.

|  | % w/w |
| --- | --- |
| Monoacetyl urea | 3.0 |
| Aluminum hydroxide (microcrystalline) | 41.5 |
| Alumina (aluminium oxide) | 2.0 |
| Glycerol | 28.0 |
| Water | 24.5 |
| Sodium lauryl sulpho acetate | 1.0 |
| Flavour | 0.7 |
| Gum tragacanth | 0.5 |
| Methyl-p-hydroxybenzoate | 0.1 |
| Saccarin | 0.05 |
| Phosphoric acid to produce a pH of 6.5 to 7.5 | q.s. |

EXAMPLE 9

This example illustrates the formulation of a skin milk.

The following ingredients were blended in order to form a skin milk.

|  | % w/w |
| --- | --- |
| Glyceryl monomyristate | 3 |
| Isopropyl isostearate | 8 |
| Oil | 3 |
| Monoacetyl urea | 2 |
| Carbopol 941 | 0.2 |
| TEA | 0.15 |
| N-methyl glucamine | 4 |
| Water | to 100 |

What is claimed is:

1. A composition for the topical treatment of living human skin which comprises from about 1% to about 20% by weight of mono acetyl urea together with an amount of N-methyl glucamine as a cosmetically acceptable vehicle sufficient to solubilize the mono acetyl urea.

2. A method for moisturizing living human skin which comprises applying to the skin a moisturizing amount of the composition as defined in claim 1.

* * * * *